United States Patent [19]

Courtney et al.

[11] Patent Number: 5,087,613
[45] Date of Patent: Feb. 11, 1992

[54] HIRUDIN VARIANTS

[75] Inventors: Michael Courtney, Geudertheim; Eric Degryse, Strasbourg; Gérard Loison, Toulouse, all of France

[73] Assignee: Transgene S.A., Courbevoie, France

[21] Appl. No.: 320,530

[22] Filed: Mar. 8, 1989

[30] Foreign Application Priority Data

Mar. 8, 1988 [FR] France .................. 88 02925

[51] Int. Cl.$^5$ .................. C07K 7/10; A61K 37/64
[52] U.S. Cl. .................. 514/12; 530/324; 530/855; 435/69.2; 435/69.6
[58] Field of Search .................. 530/324, 855; 514/12; 435/69.2, 69.6

[56] References Cited

FOREIGN PATENT DOCUMENTS 0158564 10/1986 European Pat. Off. .
0273800 7/1988 European Pat. Off. .

OTHER PUBLICATIONS

Winter, G. "Rodesigning enzyme structure by site-directed mutagenesis . . . " Nature 299, 756-758 (10/21/82).
White A., in "Principles of Biochemistry," Sixth Ed. pp. 860-863 (1978).
Dodt, J. "Interaction of site specific hirudin variants w/ αThrombin".
Clare et al. Embo J. vol. 6, pp. 529-537 1987.

Primary Examiner—Margaret Moskowitz
Assistant Examiner—Nina Ossanna
Attorney, Agent, or Firm—Cushman, Darby & Cushman

[57] ABSTRACT

The present invention relates to hirudin variants having a modified peptide structure, relative to a parent hirudin variant. The new hirudin variants of the present invention display improve biological properties relative to the parent variant.

6 Claims, 2 Drawing Sheets

FIG. 1

|   | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 HV1 | VAL | VAL | TYR | THR | ASP | CYS | THR | GLU | SER | GLY | GLN | ASN | LEU | CYS | LEU |
| 2 HV2 | ILE | THR | TYR | THR | ASP | CYS | THR | GLU | SER | GLY | GLN | ASN | LEU | CYS | LEU |
| 3 HV3 | ILE | THR | TYR | THR | ASP | CYS | THR | GLU | SER | GLY | GLN | ASN | LEU | CYS | LEU |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| CYS | GLU | GLY | SER | ASN | VAL | CYS | GLY | GLN | GLY | ASN | LYS | CYS | ILE | LEU |
| CYS | GLU | GLY | SER | ASN | VAL | CYS | GLY | LYS | GLY | ASN | LYS | CYS | ILE | LEU |
| CYS | GLU | GLY | SER | ASN | VAL | CYS | GLY | LYS | GLY | ASN | LYS | CYS | ILE | LEU |

| 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| GLY | SER | ASP | GLY | GLU | LYS | ASN | GLN | CYS | VAL | THR | GLY | GLU | GLY | THR | PRO | LYS |
| GLY | SER | ASN | GLY | LYS | GLY | ASN | GLN | CYS | VAL | THR | GLY | GLU | GLY | THR | PRO | ASN |
| GLY | SER | GLN | GLY | LYS | ASP | ASN | GLN | CYS | VAL | THR | GLY | GLU | GLY | THR | PRO | LYS |

| 48 | 49 | 50 | 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| PRO | GLX | SER | HIS | ASN | ASP | GLY | ASP | PHE | GLU | GLU | ILX | PRO | GLU | GLU | TYR | LEU | GLN |
| PRO | GLU | SER | HIS | ASN | ASN | GLY | ASP | PHE | GLU | GLU | ILX | PRO | GLU | GLU | TYR | LEU | GLN |
| PRO | GLN | SER | HIS | ASN | GLN | GLY | ASP | PHE | GLU | PRO | ILX | PRO | GLU | ASP | TYR | ASP | GLU |

↓ 64 65 66
ALA 63

1. From DODT and al. FEBS LETTERS 1984 165, 180-183.
2. From HARVEY and al. Proc. Natl. Acad. USA 1986 83, 1084-1088
3. From DODT and al. Biol. Chem. Hoppe-Seyler 1986 367, 803-811.

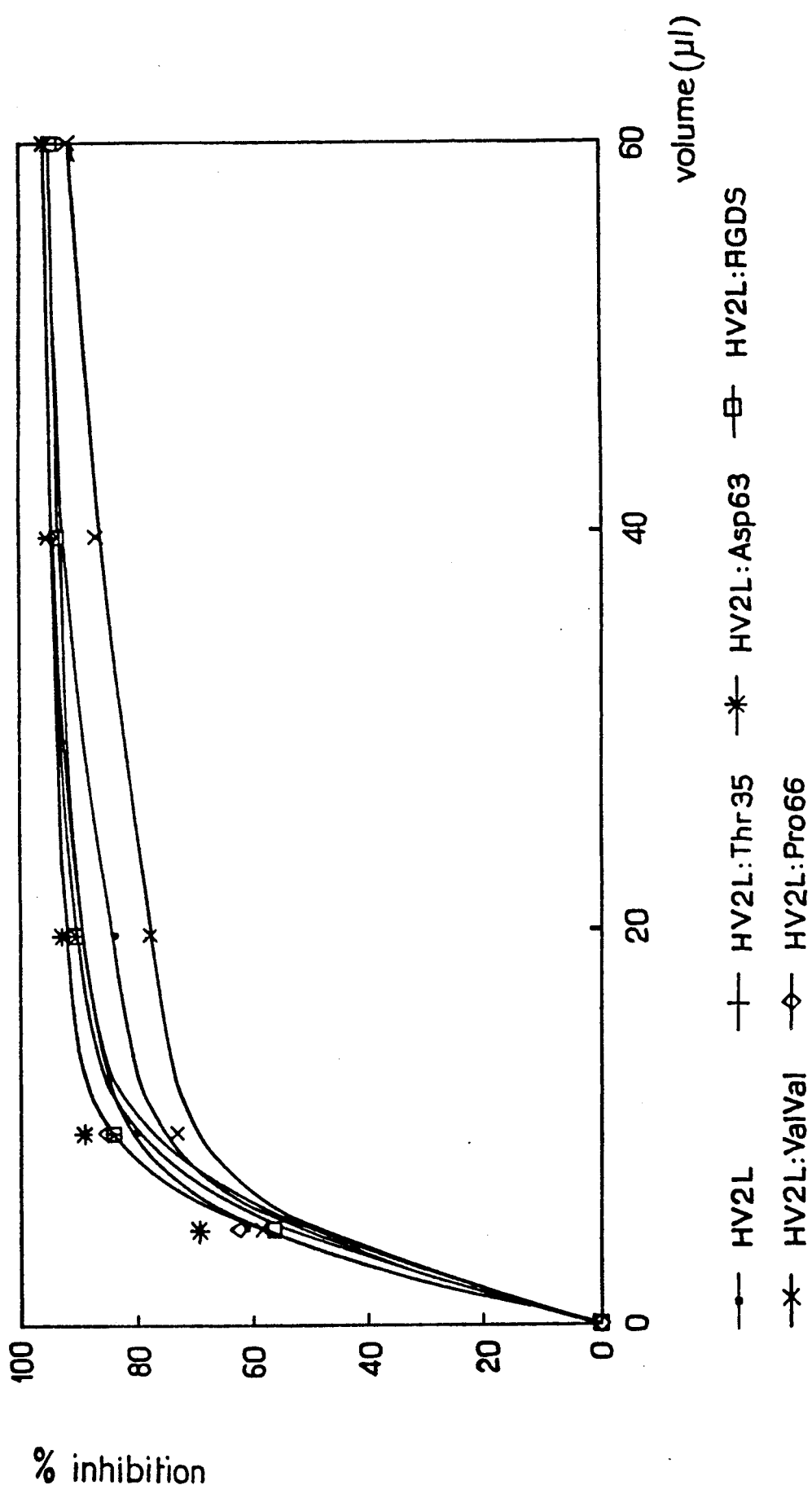
FIG_2

HIRUDIN VARIANTS

The present invention relates to hirudin variants, to their uses and to the methods for obtaining them.

Natural hirudin is a mixture of peptides of 65 and 66 amino acids secreted in very small amounts by the salivary glands of the medicinal leech (Markwardt 1970; Peterson et al. 1976; Chang 1983; Dodt et al. 1984, 1985, 1986; Harvey et al. 1986). The first variant described, HV1 (Dodt et al. FEBS Letters 1984, 165, 180–183), corresponds to the hirudin which is isolated from the body of the leech; the second, HV2 (Harvey et al. Proc. Natl. Acad. Sci. USA, 1986) 83; 1084-1088 differs from the first by 9 amino acids, and the third (Dodt et al. 1986) is identical to HV2 as far as the serine$^{32}$, but differs by 10 amino acids in the C-terminal portion, which further comprises an additional amino acid (Ala$^{63}$). This third variant is designated HV3 (Dodt et al. Biol. Chem. Hoppe-Seyler 1986 367, 803–811). The structures of these three variants are depicted in FIG. 1.

The sequences of these natural variants contain 65 or 66 amino acids and may be regarded as two domains: a globular N-terminal portion which contains 3 disulfide bridges, and an acidic C-terminal portion which displays a homology with the site of cleavage by thrombin in the prothrombin molecule. This homology has led to the suggestion that the region surrounding position 47 could be a site of binding of hirudin to thrombin. For this reason, the Applicant has already described, in European Patent Application No. 87.402696.6, hirudin variants which contain an amino acid different from the amino acid present in the natural form at position 47. In particular, the variant HV2 (Lys$^{47}$) has been described as displaying improved kinetics of thrombin inhibition and greater antithrombotic activity than the unmodified molecule.

The subject of the present invention is new hirudin variants displaying improved biological properties.

In the first place, in order to improve the pharmacokinetic profile of the hirudin molecule in order to prolong its action in vivo and thereby reduce the therapeutic dose needed, it is possible to introduce covalent post-translational modifications, in particular hydrocarbon side chains which can mask the sites of the polypeptide responsible for the elimination of the molecule from the circulation.

For this reason, one or more glycosylation sites capable of promoting the addition of hydrocarbon chains are created on the molecule. Glycosylation often takes place on Asn residues at specific recognition sites Asn-X-Thr or Asn-X-Ser and, on hirudin, a possible modification consists in replacing the amino acid Lys$^{35}$ by the amino acid Thr$^{35}$, leading to the sequence Asn$^{33}$-Gly$^{34}$-Thr$^{35}$.

Moreover, natural hirudin does not possess specific sites of recognition by blood cell surface receptors. To modify the in vivo mode of action of hirudin, it appeared advantageous to introduce into the hirudin molecule a sequence Arg-Gly-Asp-Ser (RGDS) to permit better interaction with cell surface receptors. This RGDS sequence is present in fibrinogen on a site involved in binding with the platelet receptor GpIIb/-IIIa. Recent work (Ruggeri et al., 1986) has made it possible to demonstrate that fibrinogen - GpIIb/IIIa interaction was necessary for platelet aggregation, and that peptides containing an RGDS sequence inhibited platelet aggregation.

Finally, in the case where hirudin is prepared by genetic engineering techniques, in particular by expression and secretion using Saccharomyces cerevisiae yeast, it was found that, during its production, the hirudin could undergo undesirable degradations at the C-terminal end through the effect of carboxypeptidases. To reduce these degradations, the invention proposes modifying the C-terminal end of the molecule by adding one or more amino acids, for example proline, thereto.

The object of the invention is hence hirudin variants, wherein the peptide structure of these variants contains, relative to the parent HV variants, one of the following modifications:

in at least one site Asn-X-Y of HV where X is any amino acid, Y is chosen from Ser or Thr;
a sequence Arg-Gly-Asp-Ser replaces an amino acid sequence;
at least one additional amino acid is added at the C-terminal end;

the parent HV variants are chosen from: HV1, HV2, HV3, HV2 (Val$^1$, Val$^2$), HV1 (AA$^{63}$), HV2 (AA$^{63}$), HV3 (AA$^{64}$), HV2 (Val$^1$, Val$^2$, AA$^{63}$), HV2 (Lys$^{47}$), HV2 (Val$^1$, Val$^2$, Lys$^{47}$), HV2 (Lys$^{47}$, AA$^{63}$), HV2 (Val$^1$, Val$^2$, Lys$^{47}$, AA$^{63}$), and AA is chosen from Glu and Asp.

The parent variants may be obtained according to the methods described in European Patent Application 87.402696.6 in the name of the Applicant.

The invention relates especially to a family of hybrid molecules in which HV is HV2 (Lys$^{47}$) and which, in addition to at least one of the above modifications, or as a sole modification, contain the amino acids Val$^1$-Val$^2$ in place of the amino acids Ile$^1$-Thr$^2$.

The variants in question are, in particular: HV2 (Lys$^{47}$), HV2 (Lys$^{47}$, AA$^{63}$), HV2 (Val$^1$, Val$^2$, Lys$^{47}$), HV2 (Val$^1$, Val$^2$, Lys$^{47}$, AA$^{63}$).

One of the sites which is more especially usable for performing the first modification is located at amino acids 33 to 35 of HV2, replacing (Lys$^{35}$) by (Thr$^{35}$) or (Ser$^{35}$).

One of the sites which is more especially usable for performing the second modification is located on amino acids 33 to 36, and the variants (Arg$^{33}$, Asp$^{35}$, Ser$^{36}$) are the most advantageous, especially the HV2 variant (Lys$^{47}$).

Although it is possible to add any amino acid at the C-terminal end, it is preferable to use proline, for example the variant HV2 (Lys$^{47}$, Pro$^{66}$).

Finally, to obtain stronger thrombin-inhibitory activity, improved pharmacokinetic properties, greater stability and an improved antithrombotic action compared with the variant HV2 (Lys$^{47}$), which has been described by the Applicant in European Patent Application No. 87.402696.6, the following variants are of great interest:

```
A B TYR THR ASP CYS THR GLU SER GLY GLN
ASN LEU CYS LEU CYS GLU GLY SER ASN VAL
CYS GLY LYS GLY ASN LYS CYS ILE LEU GLY
SER ASN GLY LYS GLY ASN GLN CYS VAL THR
GLY GLU GLY THR PRO LYS PRO GLU SER HIS
ASN ASN GLY ASP PHE GLU GLU ILE PRO GLU
GLU C LEU GLN
``` in which A-B denotes Ile-Thr or Val-Val and C denotes Glu or Asp.

In effect, sulfation of the tyrosine$^{63}$ possibly constitutes an important difference between natural hirudin and the hirudin obtained by genetic recombination, as suggested by the kinetic studies of Stone and Hofsteenge (1986).

For this reason, in the above derivatives, (Tyr$^{63}$) was replaced by Glu or Asp.

The above modifications can occur simultaneously. Among the variants in question, the following should be given preferential mention:

HV2 (Lys$^{47}$, Asp$^{63}$)
HV2 (Lys$^{47}$, Asn$^{33}$-Gly$^{34}$-Thr$^{35}$)
HV2 (Lys$^{47}$, Arg$^{33}$, Asp$^{35}$, Ser$^{36}$)
HV2 (Lys$^{47}$, Pro$^{66}$)

as well as the variants:

(Val$^{1}$-Val$^{2}$) HV2 (Lys$^{47}$)
(Val$^{1}$-Val$^{2}$) HV2 (Lys$^{47}$, Asp$^{63}$)
(Val$^{1}$-Val$^{2}$) HV2 (Lys$^{47}$, Thr$^{35}$)
(Val$^{1}$-Val$^{2}$) HV2 (Lys$^{47}$, Arg$^{33}$, Asp$^{35}$, Ser$^{36}$)
(Val$^{1}$-Val$^{2}$) HV2 (Lys$^{47}$, Pro$^{66}$).

The different variants which have retained the Tyr$^{63}$ can be used in sulfated or non-sulfated form. This sulfation may be obtained chemically or biologically.

The present invention encompasses the biological and/or chemical methods by means of which the above-mentioned variants may be prepared.

These variants can, in effect, be obtained by synthesis or partial synthesis and/or by the known techniques of genetic engineering.

Thus, for example, the cloning and expression of the sequence coding for HV2 and production of the corresponding hirudin from yeasts have been described in the publication of European Patent EP-A-200,655.

The variants according to the invention may be obtained by equivalent techniques, after the sequence coding for HV2 has been modified, for example by directed mutagenesis.

In particular, by in vitro directed mutagenesis, HV2 variants have been constructed in which the asparagine$^{47}$ is replaced by a lysine and in which either the lysine$^{35}$ is replaced by a threonine, or the asparagine$^{33}$ is replaced by an arginine, the lysine$^{35}$ by an asparate and the glycine$^{35}$ by a serine, or the tyrosine$^{63}$ is replaced by an aspartate, or alternatively the sequence Ile$^{1}$-Thr$^{2}$ is replaced by Val$^{1}$-Val$^{2}$.

In particular, it is possible to use functional expression blocks in yeast as described in Patent Application EP-A-200,655, and in which the hirudin sequence codes for the above variants; these functional DNA blocks can be carried by a plasmid vector.

To direct the expression and secretion by yeast of the genes corresponding to the different variants, the genes are integrated in a vector for yeast which preferably comprises the following elements, which have been described in Application EP-A-200,655:

the origin of replication of the yeast to 2 μ plasmid, the ura3 gene,
an origin of replication in E. coli and a marker for resistance to an antibiotic,
a transcription promoter, the leader sequence and the prepro sequence for the precursor of the alpha factor, fused in phase upstream from the coding sequence for the hirudin variant,
the transcription terminator of the yeast PGK gene, which will be placed downstream from the gene for the said variant.

The invention also relates to the yeasts transformed by these vectors or by this functional DNA block, and to their application to the preparation of hirudin variants.

In particular, the invention relates to a method for preparing a hirudin variant, by fermentation of a yeast according to the invention and recovery of the hirudin produced in the culture medium in mature form or in the form of a precursor which can be matured in vitro.

The techniques employed have already been described in greater detail in Patent Applications EP-A-200,655 and EP-87.401649.6.

The hirudin variants thereby obtained can be used as described in Patent Application EP-A-200,655, as a thrombin inhibitor both in vivo and in vitro.

In particular, these variants can be used in pharmaceutical compositions, alone or in combination with other active principles, or alternatively in the context of tests or diagnosis, in vitro or in vivo. In the latter case, it can be advantageous to label the variants, for example by radioactive, fluorescent, enzyme or other labeling.

The present invention is illustrated by the examples which follow, with the aid of FIG. 1 which shows the sequences of the 3 natural variants of hirudin, and FIG. 2 which shows the percentage inhibition of the proteolytic activity of thrombin on chromozyme in terms of the volumes of supernatants of yeast cultures producing the variants of hirudin HV2 (Lys$^{47}$), designated HV2L.

EXAMPLE 1

Production of mutated genes coding for variants of hirudin HV2 (Lys$^{47}$), by in vitro directed mutagenesis.

To perform an in vitro direct mutagenesis, the DNA fragment which it is desired to modify is cloned into the replicative form of a single-stranded phage M13; the genome of the recombinant phage is isolated and hybridized with a synthetic oligonucleotide which carries the mutated sequence. This oligonucleotide serves as a primer for the synthesis of the complementary strand, and the DNA, thereby rendered double-stranded, is used for transforming a receptor bacterium which will produce the phage carrying the desired mutation (Zoller and Smith, 1983).

The hirudin HV2 coding sequence was manipulated to make it into a functional "expression cassette" in yeast, and to provide for the secretion of the synthesized protein. To this end, a DNA segment coding for the prepro sequence of the α-pheromone of yeast was placed upstream from the gene. This construction is referred to as pTG1833.

The cassette for the expression of hirudin was recovered in the form of a PstI-BglII fragment and introduced into a phage M13 derivative, M13TG131 (Kieny et al. 1983), to perform the subsequent mutageneses therein.

A mutagenesis was performed in the prepro sequence to create a HindIII site which will permit the fusion of the hirudin coding sequences and the ready exchange of the latter with the various mutated sequences, while preserving the reading frame and providing for the correct maturation of the synthesized protein.

The mutated sequence is as follows:

⟵——modified prepro sequence——⟶|⟵——hirudin——⟶

. . . Glu Ala Val Ser Leu Asp Lys Arg Ile Thr . . .

. . . GAA GGG GTA AGC TTG GAT AAA AGA ATT ACG . . .
                HindIII

A mutation was introduced into the HV2 coding sequence to replace the Asn; by a Lys$^{47}$. This mutagenesis was performed with the following oligonucleotide:

5' CTTTCAGGTTTCGGTGTAC 3'

The phage M13 derivative carrying the expression cassette with these 2 mutations, referred to as M13TG1945, will serve as a primer for all the following mutageneses.

To induce further mutations in the HV2 coding sequence, the following oligonucleotides were used:

TG1152: 5' CTAATGGAACTGGCAACCA 3'
TG1153: 5' TGGGTTCTAGAGGAGACAGCAACCAATG 3'
TG1154: 5' CAGAAGAAGATTTACAATG 3'
TG1155: 5' GATAAAAGAGTTGTTTATACAGACT 3'
TG1156: 5' TATTTACAACCATAAATGAAAGAA 3'

The mutated sequences correspond, respectively, to the following variants:

HV2 (LYS$^{47}$, Thr$^{35}$)
HV2 (Lys$^{47}$, Arg$^{33}$, Asp$^{35}$, Ser$^{36}$)
HV2 (Lys$^{47}$, Asp$^{63}$)
HV2 (Lys$^{47}$, Val$^{1}$, Val$^{2}$)
HV2 (Lys$^{47}$, Pro$^{66}$)

The mutagenesis was performed under the following conditions:

120 picomoles of each oligonucleotide were phosphorylated in 100 μl of reaction medium, and approximately 20 picomoles of phosphorylated oligonucleotide were hybridized with 1 picomole of phage M13TG1919 single-stranded DNA in 25 microliters of hybridization buffer.

Afer hybridization, the mixture of DNAs was subjected to the action of Klenow polymerase and to phage T4 ligase. Each mixture thus treated was used for transfecting E. coli strain 71/18 (mut L) on a lawn of indicator bacteria JM103 (Messing et al. 1981). The infected cells are identifiable, since they form slower-growing plaques; the colonies were subcultured on complete medium and then transferred onto Whatman 540 paper for the purpose of screening the cells possessing the mutated phages.

The identification of the phages carrying the mutated sequence is accomplished by in situ hybridization with the oligonucleotide which was used for the mutagenesis. The following phages carrying mutated sequences were obtained:

M13TG1946 ⟶ HV2 (Lys$^{47}$, Thr$^{35}$)

M13TG1947 ⟶ HV2 (Lys$^{47}$, Arg$^{33}$, Asp$^{35}$, Ser$^{36}$)

M13TG1948 ⟶ HV2 (Lys$^{47}$, Asp$^{63}$)

M13TG1949 ⟶ HV2 (Lys$^{47}$, Val$^{1}$, Val$^{2}$)

M13TG1950 ⟶ HV2 (Lys$^{47}$, Pro$^{66}$)

EXAMPLE 2

Transfer of the mutated genes into an expression/secretion vector and transformation of the host yeasts The expression/secretion vector pTG2835 comprises the following elements:

1. The origin of replication and the gene for resistance to ampicillin of plasmid pBR322, permitting the multiplication of the plasmid and its selection in E. coli.
2. The origin of replication of the yeast 2 μ plasmid and the yeast ura3 gene as a selection marker in a ura3 yeast strain.
3. Another selection marker, the yeast leu2 gene which can be used to complement a defective leu2 gene on the host strain.
4. The transcription promoter of the gene for the α-pheromone of yeast and the transcription terminator of the yeast PGK gene.
5. The prepro sequence of the gene for the α-pheromone of yeast, manipulated so as to create a HindIII site therein permitting the fusion of the hirudin gene, in phase and in such a way as to provide for the correct maturation of the synthesized protein.

The hirudin coding sequences carrying the selected mutations and carried by the phages M13TG1946, 1947, 1948, 1949 and 1950, were recovered in the form of HindIII fragments and reintroduced into the vector pTG2835 to give the following plasmids:

pTG2982 ⟶ HV2 (Lys$^{47}$, Thr$^{35}$)

pTG2983 ⟶ HV2 (Lys$^{47}$, Asp$^{63}$)

pTG2988 ⟶ HV2 (Lys$^{47}$, Arg$^{33}$, Asp$^{35}$, Ser$^{36}$)

pTG2989 ⟶ HV2 (Lys$^{47}$, Val$^{1}$, Val$^{2}$)

pTG2990 ⟶ HV2 (Lys$^{47}$, Pro$^{66}$)

An S. cerevisiae yeast strain TGY1sp4 (matα ura3.251.373.38 his03.11.15) was transformed by these different plasmids.

The antithrombin activity of the different hirudin variants produced by these strains was compared (see FIG. 2).

20 ml of culture (YNBG+0.5% casamino acids) at an OD$_{660}$ of 0.02 was seeded with each strain. After 48 h of agitation at 30° C., the cultures are centrifuged (5,000 rpm, 5 min) and the supernatants are assayed. A culture of TGY1sp4 pTG881 (plasmid not carrying a sequence coding for HV2) is used as a control. The activity of the crude supernatants is measured by their inhibitory effect on thrombin activity (proteolytic activity on a synthetic substrate, chromozyme TH Boehringer Mannheim). The percentage inhibition in terms of the volumes of supernatant is given in FIG. 2.

This study shows clearly that the modifications of the hirudin sequence do not cause any loss in antithrombin activity, or any loss in productivity in yeast.

The use of these new molecules in vivo as an antithrombotic agent can hence be envisaged.

REFERENCES

Chang, J. Y. FEBS Letters 164, 307–313 (1983).

Dodt. J., Mueller, H. P., Seemüller, U, and Chang, J. Y. FEBS Letters 165, 180–184 (1984).

Dodt. J., Seemüller, U., Mascheler, R. and Fritz, H. Biol. Chem. Hoppe-Seyler 366, 379–385 (1985).

Dodt. J., Machleidt, W., Seemüller, U., Maschler, R. and Fritz, H. Biol. Chem. Hoppe-Seyler 367, 803–811 (1986).

Harvey, R. P., Degryse, E., Stefani, L., Schamber, F., Cavenave, J. P., Courtney, M., Tolstoshev, P. and Lecocq, J. P. Proc. Natl. Acad. Sci. USA 83, 1084–1088 (1986).

Kieny, M. P., Lathe, R. and Lecocq, J. P. Gene 26, 91–99 (1983).

Markwardt, F. Methods Enzymol. 19, 924–932 (1970).

Messing, J., Crea, R. and Seeburg, P. H. Nucl. Acids Res. 9, 309 (1981).

Petersen, T. E., Roberts, H. R., Sottrup-Jensen L. and Magnusson, S. Protides, Biol., Fluids, Proc. Colloq. 23, 145–149 (1976).

Ruggeri, Z. M., Houghten, R. A., Russell, S. R. and Zimmerman, T. S. Proc. Natl. Acad. Sci. USA 83, 5708–5712 (1986).

Stone, S. R. and Hofsteenge, J. Biochem. 25, 4622–4628 (1986).

Zoller, M. J. and Smith, M. N. Methods in Enzymol. 100, 469 (1983).

We claim:

1. A hirudin variant hirudin Lys$^{47}$, Arg$^{33}$, Asp$^{35}$, Ser$^{36}$ or hirudin variant 2Lys$^{47}$, Arg$^{33}$, Asp$^{35}$, Ser$^{36}$.

2. The variant according to claim 1, wherein said variant is hirudin variant 2Lys$^{47}$, Arg$^{33}$, Asp$^{35}$, Ser$^{36}$.

3. The variant according to claim 1 wherein said variant is sulfated.

4. A pharmaceutical composition comprising as an active ingredient said variant according to claim 1 in an amount sufficient to exert an anticoagulatory effect, together with a pharmaceutically acceptable carrier.

5. A method of exerting an anticoagulation effect in a patient comprising administering to said patient an amount of said variant according to claim 1 sufficient to exert said effect.

6. A method of exerting a thrombin inhibitory effect in a patient comprising administering to said patient an amount of said variant according to claim 1 sufficient to exert said effect.

* * * * *